(12) United States Patent
Namm et al.

(10) Patent No.: US 10,575,775 B2
(45) Date of Patent: Mar. 3, 2020

(54) METHOD AND APPARATUS FOR MONITORING HYDRATION USING A PORTABLE COMMUNICATION DEVICE

(71) Applicant: MOTOROLA SOLUTIONS, INC, Chicago, IL (US)

(72) Inventors: Joseph C Namm, Plantation, FL (US); Melanie A King, Hollywood, FL (US)

(73) Assignee: MOTOROLA SOLUTIONS, INC., Chicago, IL (US)

(*) Notice: Subject to any disclaimer, the term of this patent is extended or adjusted under 35 U.S.C. 154(b) by 332 days.

(21) Appl. No.: 15/338,599

(22) Filed: Oct. 31, 2016

(65) Prior Publication Data

US 2018/0116590 A1    May 3, 2018

(51) Int. Cl.
*A61B 5/00* (2006.01)
*A61B 5/083* (2006.01)
*A61B 5/145* (2006.01)
*G08B 21/04* (2006.01)

(52) U.S. Cl.
CPC ............ *A61B 5/4875* (2013.01); *A61B 5/083* (2013.01); *A61B 5/14517* (2013.01); *A61B 5/4845* (2013.01); *A61B 5/6806* (2013.01); *A61B 5/6898* (2013.01); *A61B 5/746* (2013.01); *A61B 5/747* (2013.01); *G08B 21/0461* (2013.01); *A61B 2503/20* (2013.01); *A61B 2560/0242* (2013.01)

(58) Field of Classification Search
CPC ... B63C 11/18; G08B 21/0461; A61B 5/4875; A61B 5/083; A61B 5/14517; A61B 5/4845; A61B 5/6806; A61B 5/6898; A61B 5/746; A61B 5/747; A61B 2560/0242; A61B 2503/20
See application file for complete search history.

(56) References Cited

U.S. PATENT DOCUMENTS

| | | | |
|---|---|---|---|
| 6,992,580 B2 | 1/2006 | Kotzin et al. | |
| 8,989,834 B2 | 3/2015 | Ho et al. | |
| 9,165,117 B2 | 10/2015 | Teller et al. | |
| 2006/0125623 A1* | 6/2006 | Appelt | A61B 5/02055 340/521 |
| 2014/0221792 A1* | 8/2014 | Miller | A61B 5/4875 600/309 |
| 2014/0249388 A1 | 9/2014 | Howell et al. | |
| 2016/0080888 A1 | 3/2016 | Kreitzer et al. | |

FOREIGN PATENT DOCUMENTS

WO      2014114847 A1    7/2014

* cited by examiner

*Primary Examiner* — Christopher Koharski
*Assistant Examiner* — Jessandra F Hough
(74) *Attorney, Agent, or Firm* — Barbara R. Doutre

(57) ABSTRACT

A portable communication device (100) automatically determines user hydration levels while the device is being transmitted. The portable communication device comprises a humidity sensor (120) located by a microphone and touch sensors (124) located on a push-to-talk (PTT) button (110). Data is gathered during PTT switch activation (112). No additional steps are required by the user. Alerts (140) are provided when predetermined dehydration thresholds are approached.

10 Claims, 4 Drawing Sheets

METHOD AND APPARATUS FOR MONITORING HYDRATION USING A PORTABLE COMMUNICATION DEVICE

FIELD OF THE INVENTION

The present invention relates generally to portable communication devices and more particularly to monitoring hydration levels using a portable communication device.

BACKGROUND

Portable battery-powered communication devices, such as two-way radios, along with associated accessories are advantageous in many environments, but particularly in public safety environments, such as fire rescue. First responders operating in fire rescue environments face many challenges including working under severe high temperature, smoke-filled conditions, while carrying and wearing heavy cumbersome equipment and protective clothing. Maintaining body hydration while operating at a fire incident is thus a major concern for firefighters.

Dehydration is a leading cause of low performance and serious illness for firefighters. Past dehydration detection approaches have not proven sufficient to address the needs of today's fire rescue personnel working at fire incidents.

Accordingly, there is a need for an improved method and apparatus for monitoring hydration, particularly hydration of a firefighter during a fire incident.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments

Figure 1:
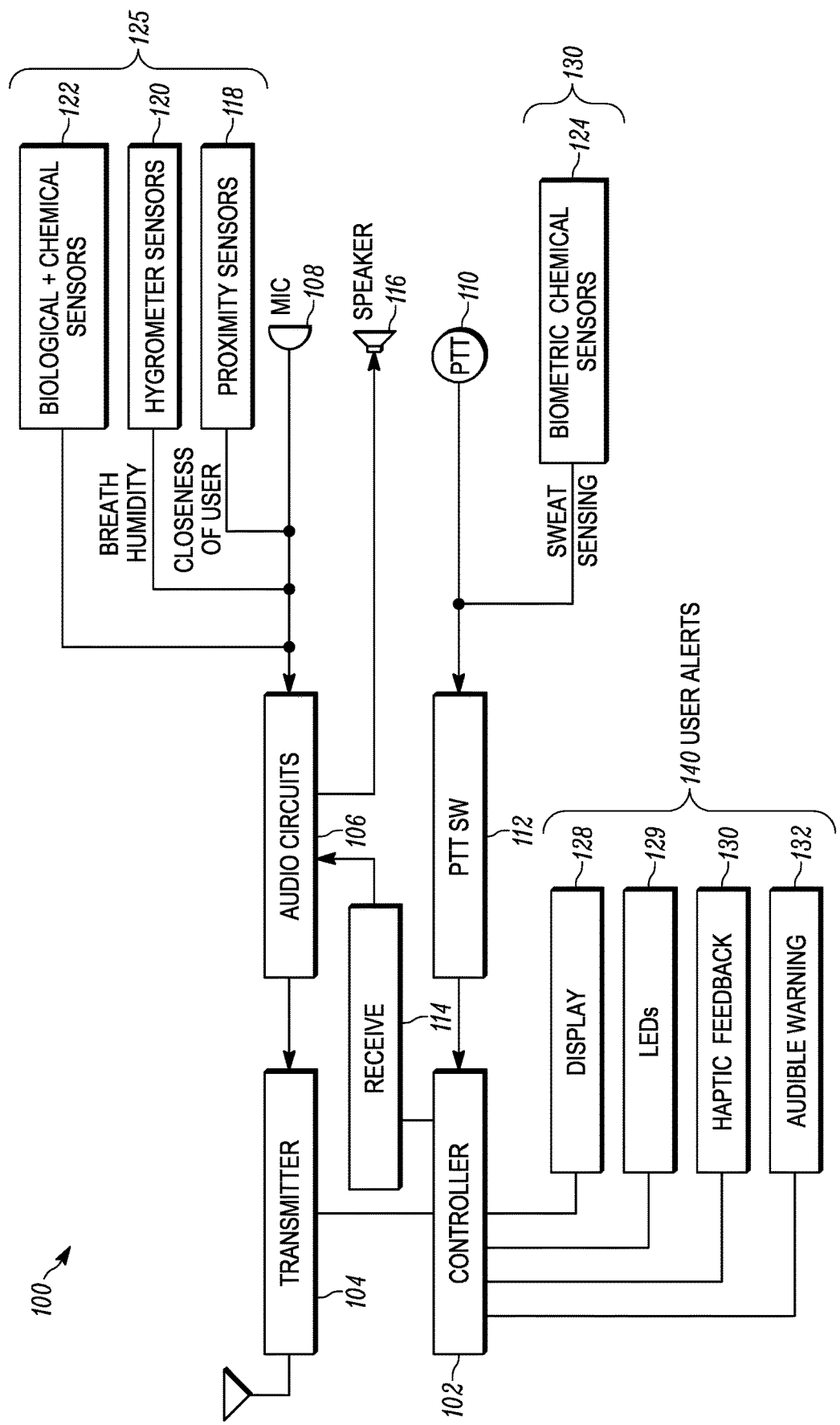
FIG. 1 is block diagram of a portable communication device having hydration monitoring capability in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Briefly, there is described herein a method and apparatus for monitoring hydration using a portable communication device. In accordance with an embodiment, the portable communication device determines hydration levels while a PTT of the portable communication device being pressed. The PTT button enables sensors on the portable communication device, including a humidity sensor located by a microphone and a touch sensor located on the push-to-talk button, the portable communication device determining user hydration levels based on data gathered by the sensors during the PTT press. In accordance with a further embodiment, the PTT enables sensors on another user-worn device at least one of which comprises a microphone having a humidity sensor proximately located thereto and skin sensors located thereon, and the portable communication device determines user hydration levels based on data gathered by the sensors of the user-worn device during the PTT press of the portable communication device.

FIG. 1 is a block diagram of a portable communication device 100 formed and operating in accordance with the various embodiments. The portable communication device 100 is a wearable, battery powered, type device that provides radio communication for public safety personnel, such as firefighters, police, search and rescue, and other individuals operating as responders to public safety incidents in which two-way radio communications are utilized. For example, the portable communication device 100 may comprise a portable public safety radio, a remote speaker microphone (RSM), and the like. The portable communication device 100 may also operate in conjunction with, and as part of, a communication system which further comprises other body-worn devices such as a smart mask and/or smart gloves formed and operating in accordance with some embodiments to be described later in accordance with fire incident events or bio-hazard events.

The portable communication device 100 comprises a controller 102, a transmitter 104, a receiver 114, audio circuits 106, microphone 108, push-to-talk switch (PTT), PTT switch 112, and speaker 116 all operating in accordance with two-way radio protocols and frequencies, for example Land Mobile Radio (LMR) radio operating over Narrowband Public Safety Frequencies.

In accordance with some of the embodiments, the portable communication device 100 further comprises a plurality of sensors 125, 130 which are responsive to the PTT switch 112 being activated by PTT button 110. The plurality of sensors 125, 130 will also be referred to as microphone breath sensors 125 and PTT skin sensors 130. In accordance with some embodiments, the microphone breath sensors 125 measure breath parameters the PTT button 110 is being pressed, and the PTT skin sensors 130 measure sweat parameters while the PTT button 110 is being pressed. In accordance with some embodiments, the measured sweat and breath parameters are combined to provide a representative user hydration level.

In accordance with some embodiments, the microphone breath sensors 125 comprise one or more hygrometer sensor(s) 120 operatively coupled to the microphone 108 for measuring humidity levels of a user's breath, when the user is speaking into the microphone during a PTT press. The microphone breath sensors 125 may further comprise chemical and biological sensors 122 co-located on or near the microphone for measuring high bacteria concentration. High bacteria concentration on the breath is known to correlate with dehydration. The plurality of microphone breath sensors 125 may further comprise proximity sensors 118 located near and operatively coupled to operation of the microphone 108 to correlate measured humidity with distance to the user. Ambient humidity measurements may be taken periodically by the hygrometer sensors 120 when the proximity sensors 118 determine that a user's mouth is not in proximity to the microphone 108 and no PTT is being pressed.

In accordance with some embodiments, the PTT sweat sensors 130 comprise a plurality of chemical and biological skin sensors 124. The plurality of chemical and biological skin sensors 124 determine sweat levels on the PTT finger while the PTT button 110 is being pressed and measure such sweat parameters potassium, sodium, and bacteria on the PTT button 110. Sweat sensor technology is available for example, in flex circuit board form with biological and chemical sensor arrays that detect glucose, lactate, sodium, potassium, and body temperature. When the sensors come into contact with sweat they generate electrical signals that are amplified and filtered, and then calibrated using skin temperature. In accordance with some embodiments, PTT sweat parameters are used in conjunction with the microphone breath parameters to determine user hydration levels.

In accordance with a further embodiment, the PTT sweat sensors 130 comprising the plurality of chemical and biological skin sensors 124 may further detect toxins which may not only impact user hydration levels but provide an indicator that a user, such as a firefighter or other public safety individual, has come under exposure to biohazardous materials and/or toxic environmental conditions. The user pressing a PTT button 110 provides an ideal opportunity for collecting user data samples over a period of time with which to generate early detection and warning of exposure to toxins. Thus, toxicity levels may also be incorporated as part of the measurements taken during PTT press of the portable communication device 100.

In accordance with some embodiments, ambient humidity can be tracked with the hygrometer sensors 120 by periodically taking ambient humidity sample readings. Hydration levels associated with an individual are measured by breath humidity at the microphone and sweat samples at the PTT button 110 while the user speaks into the microphone while pressing the PTT button 110. The proximity sensors 118 correlate measured humidity with distance to the user. A ratio of ambient humidity and user breath humidity may be calculated based on proximity to determine user hydration based on breath. In accordance with some embodiments, breath and sweat hydration levels can be combined for improved confidence levels of a user's hydration status.

In accordance with some embodiments, notifications alerting a user to moderate and/or poor hydration levels may be provided to the user through one or more notification sources. Such notification sources may comprise but are not limited to display alerts 128, LED alerts 129, haptic feedback (vibration alerts) 130, and/or audible warnings 132. The type of alert can be determined based on the type of wearable communication device being used. For example, a non-display type RSM worn on the upper shoulder could take advantage of vibration alerts or LED alerts.

Figure 2:
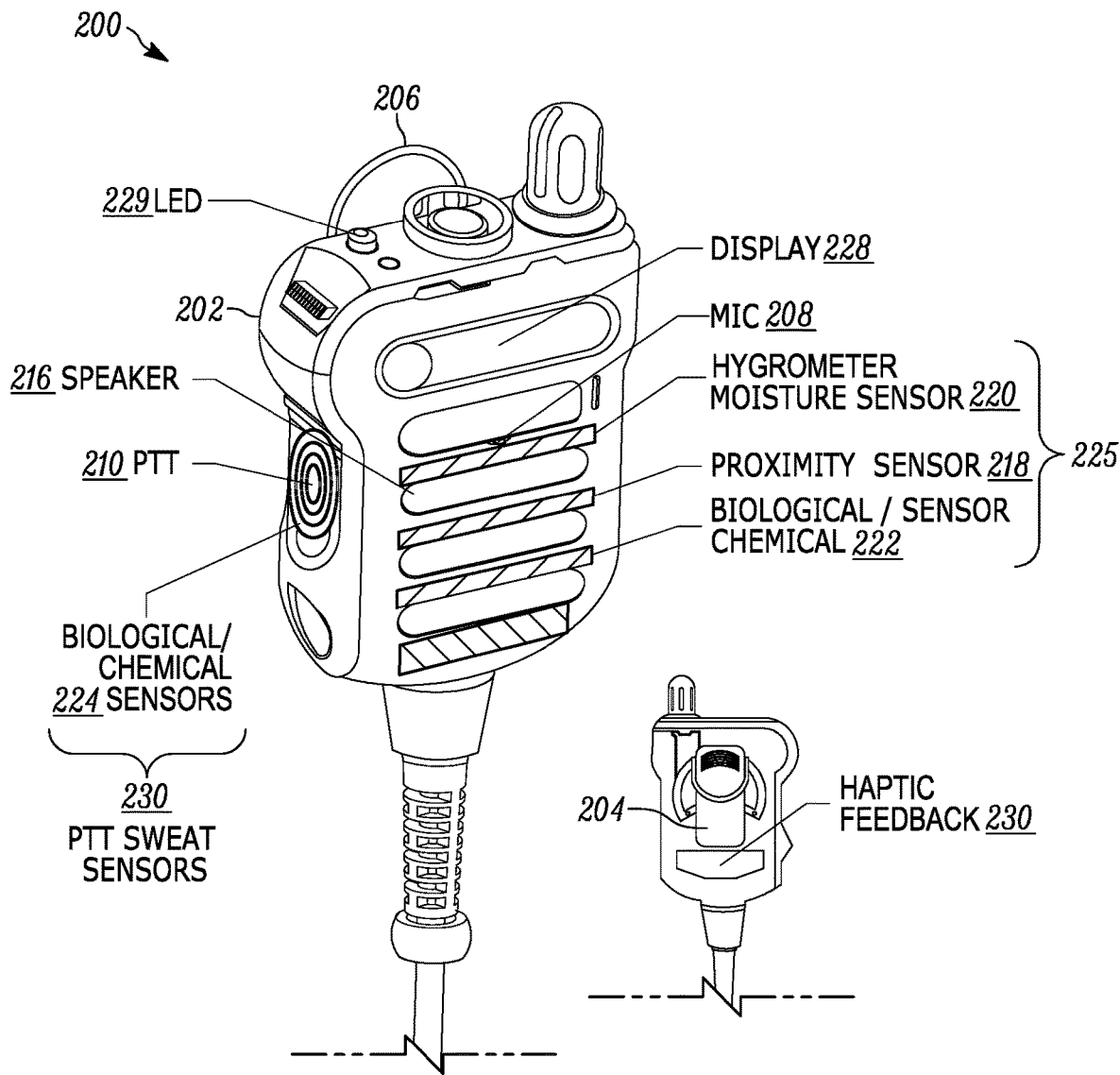
FIG. 2 is an example of a portable communication device comprising a remote speaker microphone (RSM) incorporating the hydration monitoring capability of FIG. 1 in accordance with some embodiments.

FIG. 2 is an example of a portable communication device of FIG. 1 formed and operated in accordance with some embodiments. The portable communication device is embodied here as a remote speaker microphone (RSM) 200 which operates as an accessory to a two-way radio facilitating two-way radio communications in a public safety communication system. The RSM 200 is a body-worn communication device, typically worn on the shoulder device, formed of a housing 202 clipped via a clip 204 or looped via carry loop 206 to an epaulette of a shirt or coat. The RSM 200 provides remote access to functions of a portable radio (not shown) which is typically worn at the hip. Public safety personnel, such as a police officer or firefighter, can quickly access user interface features located on the RSM, a microphone 208, a PTT button 210, and a speaker 216.

In accordance with some embodiments, the RSM 200 further comprises a plurality of microphone breath sensors 225 comprising one or more hygrometer sensors 229 located in the vicinity of the microphone 208 for measuring breath moisture when a user presses the PTT button and speaks into the microphone 208. The plurality of microphone breath sensors 225 may further comprise biological/chemical sensors 222 located in proximity of the microphone for measuring high bacteria concentration. As mentioned previously, bacteria concentration on the breath can be correlated with dehydration.

In accordance with some embodiments, the RSM 200 further comprises a plurality of PTT sweat sensors 230 comprising one or more biometric and chemical skin sensors 224 located on or about the PTT button for measuring potassium, sodium, and bacteria on the PTT button 110. The biometric and chemical skin sensors 224 may further sense for toxins which may not only impact user hydration levels but provide an indicator that a user, such as a firefighter or other public safety individual, has come under exposure to biohazardous materials and/or toxic environmental conditions.

In accordance with some embodiments when a user presses the PTT button 210 and speaks into the microphone to transmit an audio signal, the audio input into the microphone 208 is a hydration level is automatically monitored by gathering breath sample data and sweat sample data while the PTT button 210 is being pressed. The gathered breath and sweat sample data is compared to previous breath and sweat data to determine a hydration level. The hydration level may further be increased in confidence levels by comparing ambient levels correlating with proximity measurements of the user if desired. A user alert is then generated in response to the hydration level reaching a predetermined dehydration threshold.

In accordance with some embodiments notifications alerting a user to moderate and/or poor hydration levels may be provided through one or more notification sources, such as display alerts at display 228, haptic feedback (vibration alerts) at haptic feedback 230, LED alerts at LED 229, and/or audible warnings at speaker 216. The type of alert can be determined based on the type of wearable communication device being used. For example, a non-display type RSM worn on the upper shoulder could take advantage of vibrational alert or an LED alert.

Figure 3:
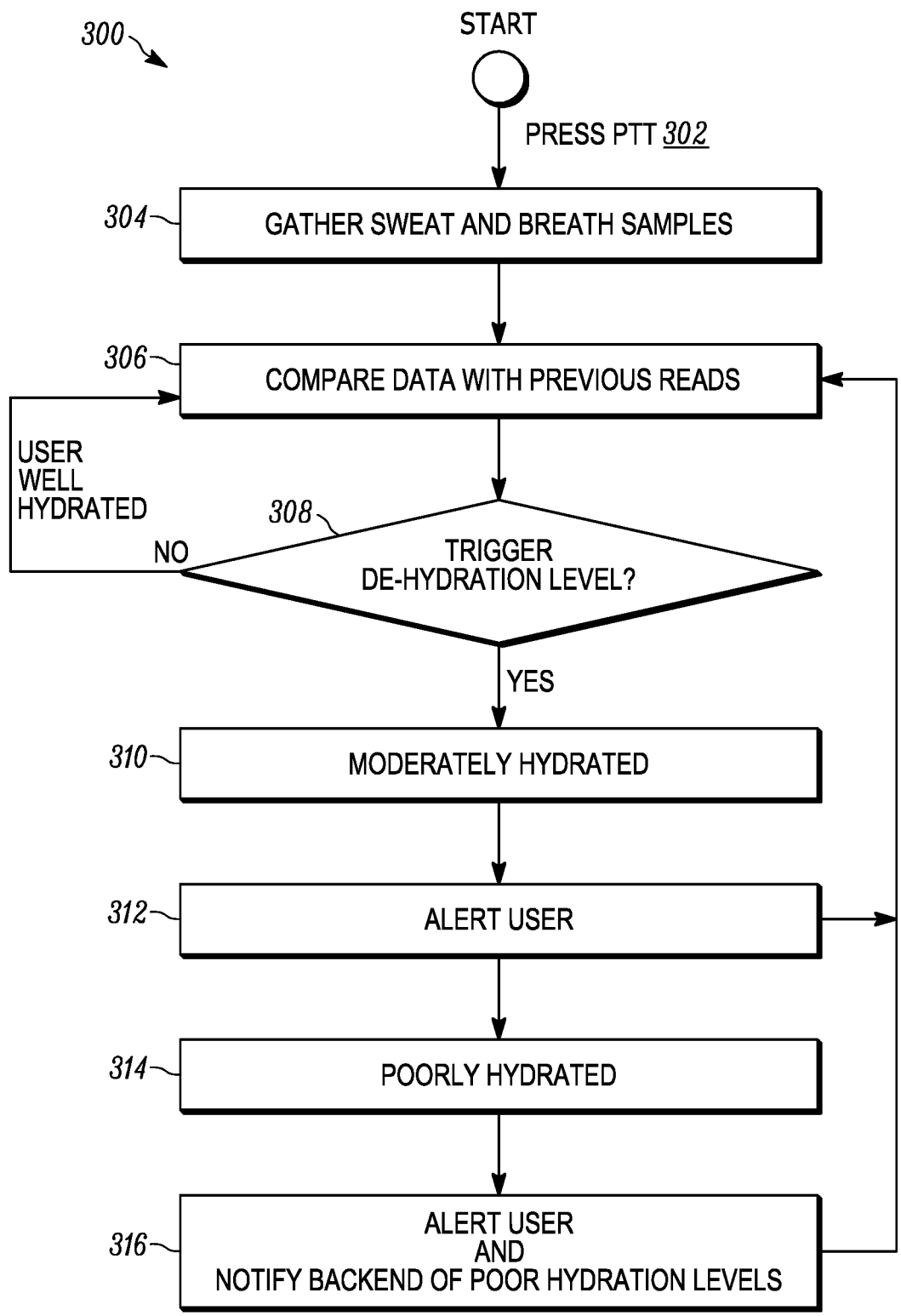
FIG. 3 is a method for monitoring hydration levels using a portable communication device in accordance with some embodiments.

FIG. 3 is a method 300 for monitoring hydration levels using a portable communication device in accordance with some embodiments. Method 300 begins at 302 by pressing a push-to-talk (PTT) button of a portable communication device. Breath sample data and sweat sample data are gathered at 304, while the PTT is being pressed. The gathered breath and sweat sample data is compared to previous breath and sweat data at 306 to determine a hydration level. The hydration level is checked to determine if a dehydration level has been triggered at 308. When no dehydration level has been triggered, the user is considered well hydrated, and the method returns to 306 to compare and check for trigger threshold levels at 308.

One or more de-hydration trigger levels or thresholds may be set at 308. For example, if a first dehydration threshold is reached at 308, then a moderately hydrated condition will be indicated at 310 which will cause the portable communication device to generate a user alert at 312. Such alerts may be generated by audible, display, vibration, and/or LED alerts. The user can then rehydrate, leave the incident, or plan out the remaining operational time remaining in order to exit safely from the incident.

If a second dehydration threshold is reached at 308, a warning of poorly hydrated is alerted to the user (as triggered at a threshold at 308) then a poorly hydrated condition will be indicated at 314 and a warning notification which will cause a warning alert to be generated to the user at the portable communication device. The user will know to rehydrate and exit the incident immediately upon receiving this warning. A further warning notification will be transmitted from the portable communication device to a backend within the communication system, warning of the user/fire fighter's poorly hydrated condition. For example, a notification may be transmitted from a portable radio to the backend, such as an incident command center or a dispatch center, that firefighter ID 123 is poorly hydrated and needs immediate medical attention.

As mentioned previously, in accordance with a further embodiment toxicity levels may also be incorporated as part of the sweat sensor measurements taken during PTT press of the portable communication device. If desired toxicity level indicators can be provided as individual alerts or maintained as part of the overall hydration alert provided by method 200.

The dehydration levels shown at 310, 314 in method 200 may or may not occur in succession depending on the environment within which a first responder operates. Dependent on extreme heat conditions, severe dehydration my occur very quickly. Additional or fewer dehydration triggers may be set, and additional or fewer alerts may be generated. Output blocks have been illustrated in method 200 for simplicity rather than the use of numerous decision blocks with the understanding that the method 200 can be adjusted in accordance with the portable communication device's interaction within an overall communication system. Thus, method 200 is adaptable while still providing for automatic hydration determination during PTT press using the combination of breath and sweat thereby providing increased confidence of a user's state. The method 200 and portable communication device 100 advantageously provide for automatic hydration levels to be measured during PTT transmission without requiring a user of the portable to take any extra steps. The further automated alerts to the user provides potential life saving warnings as well as notifications to the command center provides for improved management of an incident and ability to send in resources and assistance as needed.

Figure 4:
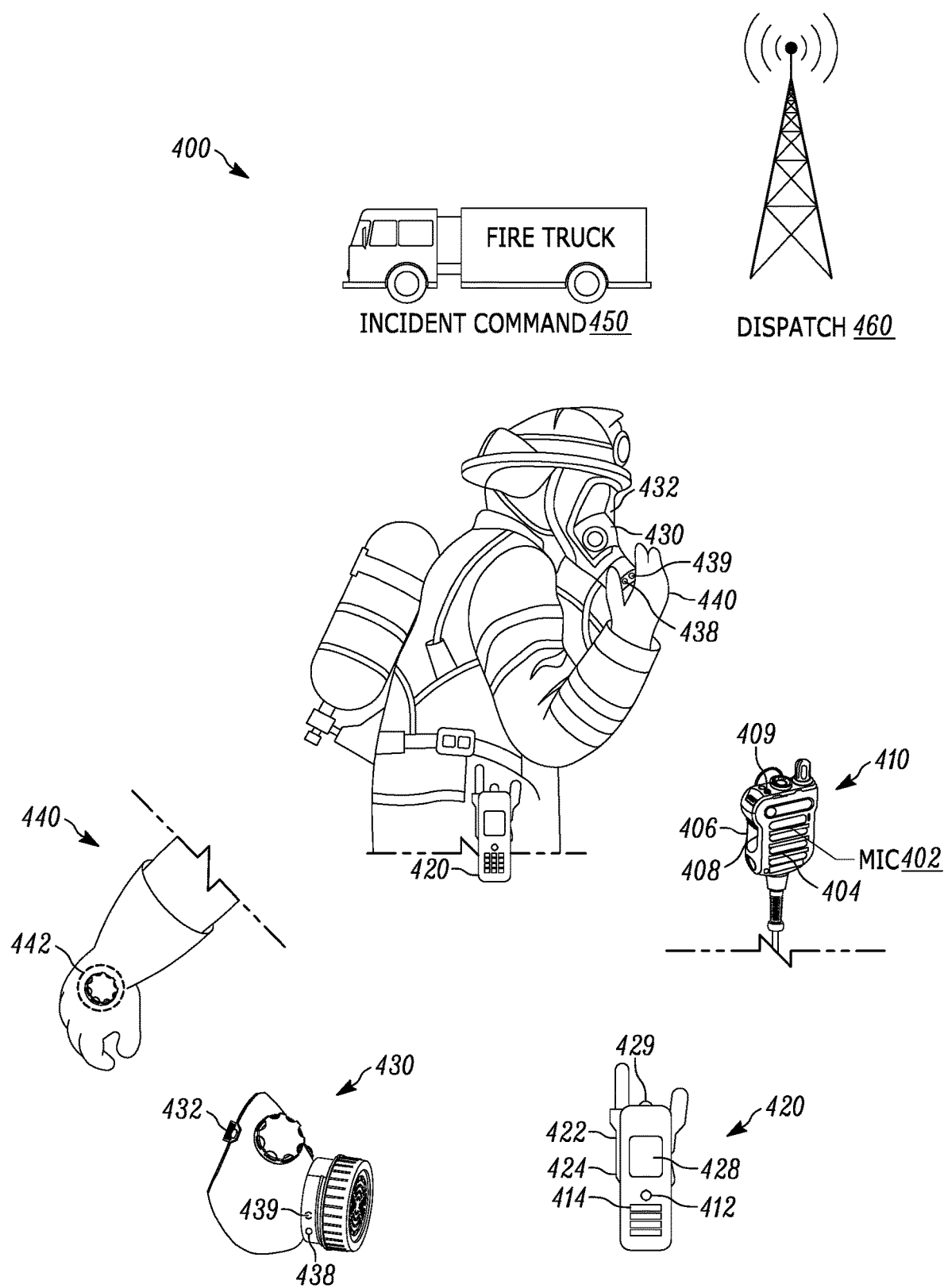
FIG. 4 is a communication system incorporating the hydration monitoring formed in accordance with some embodiments.

FIG. 4 is a simplified usage diagram of a portable communication system with examples of various portable electronic devices formed and operating in accordance with the various embodiments. The portable electronic communication devices may comprise one or more wearable communication devices utilized in fire incident environments, such as a portable radio 410, a remote speaker microphone (RSM) 420, a smart mask 430, a smart glove 440, and the like. These communication devices are presented as examples of wearable devices utilizing or the method and apparatus of the embodiments, other communication devices are also contemplated.

Portable Radio

In accordance with the some embodiments, the portable radio 420 comprises a microphone 412 and a PTT button 422 and a plurality of breath and sweat sensors 414, 424 for monitoring hydration. The hydration levels are measured based on microphone breath sensors 414 sensors being co-located with the microphone 412 for monitoring breath humidity and further enhanced by PTT skin sensors 424 located on the PTT button 422 for measuring sweat levels during PTT presses.

In a radio alone embodiment, hydration levels are measured by both breath and sweat and may be isolated or combined to provide increased confidence levels to a user 402 and/or a backend formed of a command center 450, and/or dispatch center 460. User alert examples may comprise, alerts at LED 429, audible alerts at the speaker, vibration alerts and display alerts at display 428.

Remote Speaker Microphone

Similarly for the RSM as previously described, the RSM 410 comprises a microphone 402 and a PTT button 406 and a plurality of breath and sweat sensors 408, 404 for monitoring hydration. The hydration levels are measured based on microphone breath sensors 404 sensors being co-located with the microphone 402 for monitoring breath humidity during audio input while the PTT button 406 is being pressed, and further enhanced by PTT skin sensors 408 located on the PTT button 406 for measuring sweat levels during PTT presses.

Hydration levels are measured by both breath and sweat and may be isolated or combined to provide increased confidence levels to a user and/or a backend formed of a command center 450, and/or dispatch center 460. For example LED alerts at LED 409, audible alerts at the speaker, vibration alerts and display alerts (in display RSMs).

Gloved Mode with Portable Communication Device Application

In another embodiment, a user may be wearing gloves while operating the portable communication device (RSM 410 or portable radio 420). While a PTT transmission is still activated by pressing the PTT button (RSM 410 or portable radio 420), with a gloved finger input, touch access of the user's skin to the PTT button will not take place and hence no sweat data collected. In this gloved mode operation embodiment, the PTT of the portable communication device enables sensing on another body worn device having sensing capability. While breath samples continue to be gathered from the microphone located in the RSM 410 or portable radio 420, in accordance with this gloved mode operation, sweat samples may be gathered by sweat sensors 442 integrated within gloves 440. The measured sweat data is then transferred to the portable communication device (RSM 410 or portable radio 420) over a wireless personal area network (PAN) link, for example using BLUETOOTH link or other suitable short range transfer link.

In accordance with the embodiments, hydration levels are determined at a controller of the portable communication device based on the measured breath samples taken at the microphone and the measured sweat samples taken at the glove 440 while the PTT of the portable was being pressed in accordance with the embodiments previously described.

In response to a first predetermined threshold a first alert can be provided locally to the user via an LED, display, audio feedback, or haptic feedback vibration. For example, the user may be alerted to a moderately hydrated notification. The alert may prompt the user to take in water or to a time estimate within which to seek rehydration. In response to a second predetermined hydration threshold being reach, a second alert can be provided to the user locally via the LED, display, audio feedback, and/or haptic feedback indicative of poor hydration levels. A notification of the poor hydration levels can further be transmitted from the portable communication device back to a backed, such as an indecent command center, for example set up at fire truck 450 and/or a dispatch center 460.

Gloved Mode with Smart Mask Application

In yet another embodiment, in cases where the user may be wearing gloves, the PTT of the portable communication device (RSM 410 or portable radio 420) can enable sensing on another body worn device having sensing capability, such as a smart mask 430 worn by the user, for example as a self contained breathing apparatus (SCBA) or other sealed breathing mask used in public safety type applications.

Using the portable radio 420 as an example: in gloved mode operation 440, pressing the PTT button 422 with a gloved finger input allows the user to speak into a microphone 438 integrated within the smart mask 430. Breath samples can be gathered from a microphone breath sensor 439 located in the smart mask 430. The measured breath sample data is transferred to the portable radio 420 over a wireless personal are network (PAN) link for the determination of hydration levels at a controller of the portable radio 420. Humidity levels in the sealed mask are, by default, considered to be dry, and as such there is no need to take ambient external humidity samples in the masked mode of operation.

Since this masked mode operation is also using gloved mode operation of the portable radio 420, touch access of the user's skin during pressing of the PTT button 422 will not take place. However, in accordance with the smart mask embodiment, sweat samples may be gathered by sweat sensors 432 integrated within the smart mask 430, such as along an edge or face seal perimeter of the SCBA. The measured sweat data is transferred to the portable radio 420 over a wireless personal are network (PAN) link for the determination of hydration levels at a controller of the portable radio 420.

In accordance with the embodiments, hydration levels are determined at a controller of the portable radio 420 based on the measured breath samples taken by breath humidity sensor(s) 439 near the microphone 438 within the mask 430 along with sweat samples measured by sweat sensors 432 of the mask 430, the measurements being taken while the PTT button 422 of the portable radio 420 is being pressed by a gloved user.

Accordingly, this embodiment has further shown that hydration levels can be determined at a controller of a portable communication device based on measured breath samples and sweat samples taken at collaborating devices. As such, breath samples can be measured near a microphone and sweat samples measured at sweat sensors of the collaborating device, while a PTT button is being pressed at the portable communication device.

Again, in response to a first predetermined threshold a first user alert can be generated locally at the portable radio 420 via an LED 429, display 428, audio feedback at speaker, or haptic vibration feedback. For example the user may be alerted to moderately hydrated hydration level.

In response to a second predetermined threshold a second user alert can be generated locally at portable radio 420 via the LED 429, display 428, audio feedback at speaker, or haptic vibration feedback indicating poor hydration levels. In accordance with this further embodiment, notification of poor hydration levels can further be transmitted from the portable radio 420 to a backend of the communication system 400, such as to an incident command center 450, for example set up by fire truck, or dispatch center 460 alerting other personnel within the system to the poor hydration levels of a firefighter, so that action plans can be made appropriately.

The approach provided by the various embodiments provides the advantage of being able to monitor hydration while the user is communication on the radio during transmission. Since two-way radio communication already involves the use of pressing a PTT and talking into a microphone in order to transmit, the user is not required to take any extra steps for the hydration levels to be measured. The combination of breath and sweat being used to determine hydration levels further increases the confidence levels of the user's state. Both the user and the incident commander monitoring a public safety incident can better manage the safety of individuals working in hazardous environments.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as operationally connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A portable communication system, comprising:
   a portable communication device having a controller, a microphone, and a push-to-talk (PTT) button;
   a plurality of sensors comprising a hygrometer sensor and sweat sensors, the hygrometer sensor being co-located with and operatively coupled to the microphone of the portable communication device, and the sweat sensors being located on and operatively coupled to the PTT button of the portable communication device, the hygrometer sensor measuring breath moisture and the sweat sensors measuring sweat parameters, while the PTT button is being pressed; and
   the measured breath moisture and sweat parameters providing a representative user hydration level.

2. The portable communication system of claim 1, wherein the plurality of sensors further comprise:
   Chemical and biological sensors co-located with the microphone; and
   Chemical and biological sensors located on the PTT button.

3. The portable communication system of claim 1, wherein the portable communication device comprises a remote speaker microphone (RSM) or a portable two-way radio.

4. The portable communication system of claim 1, further comprising:
   a self contained breathing apparatus (SCBA) communicatively coupled to the portable communication device over a personal area network (PAN), the SCBA comprising:
      a hygrometer sensor co-located with and operatively coupled to a microphone of the SCBA;
      a sweat sensor located in the SCBA; and
   the portable communication device receiving both measured breath moisture data from the hygrometer sensor and receiving measured sweat sensor data from the sweat sensor over the personal area network (PAN), while the PTT button of the portable communication device is being pressed; and
   the portable communication device determining the representative hydration level for a user of the SCBA based on the measured breath moisture data and measured sweat sensor data.

5. The portable communication system of claim 1, further comprising:
   a public safety fire rescue glove communicatively coupled to the portable communication device over a personal area network (PAN), the public safety fire rescue glove having a sweat sensor located therein for measuring sweat sensor data from the public safety fire rescue glove during gloved operation of the portable communication device, the measured sweat sensor data being transferred over the PAN to the portable communication device while the PTT button is being pressed; and
   the portable communication device determining the representative user hydration level based on both the measured sweat sensor data from the public safety fire rescue glove and the measured breath moisture from the hygrometer of the portable communication device.

6. A communication system, comprising:
   a portable communication device which determines user hydration levels while a push-to-talk (PTT) button of the portable communication device is being pressed, the user hydration levels being determined based on both:
      breath moisture data measured by a hygrometer sensor co-located and operatively coupled to a microphone of the portable communication device; and
      sweat sensor data measured by at least one touch sweat sensor located on and operatively coupled to the PTT button.

7. The communication system of claim 6, wherein additional sweat sensor data is gathered on a body-worn device and communicated to the portable communication device during the PTT press of the portable communication device.

8. The communication system of claim 6, wherein the touch sweat sensor further detects toxicity levels.

9. The portable communication system of claim 1, wherein breath moisture is measured when the user is speaking into the microphone during the PTT press.

10. The communication system of claim 6, wherein the breath moisture is measured when the user is speaking into the microphone during the PTT press.

* * * * *